United States Patent
Jonas et al.

(10) Patent No.: US 8,247,640 B2
(45) Date of Patent: Aug. 21, 2012

(54) HIGHLY SWELLABLE ABSORPTION MEDIUM WITH REDUCED CAKING TENDENCY

(75) Inventors: Gerd Jonas, Krefeld (DE); Richard Mertens, Krefeld (DE); Markus Frank, Tonisvorst (DE)

(73) Assignee: Evonik Stockhausen GmbH, Krefeld (DE)

( * ) Notice: Subject to any disclaimer, the term of this patent is extended or adjusted under 35 U.S.C. 154(b) by 151 days.

(21) Appl. No.: 12/718,617

(22) Filed: Mar. 5, 2010

(65) Prior Publication Data

US 2010/0160883 A1    Jun. 24, 2010

Related U.S. Application Data

(60) Division of application No. 10/424,459, filed on Apr. 25, 2003, now abandoned, which is a continuation of application No. PCT/EP2001/012315, filed on Oct. 25, 2001.

(30) Foreign Application Priority Data

Oct. 25, 2000  (DE) .................. 100 52 966

(51) Int. Cl.
*A61F 13/15*   (2006.01)

(52) U.S. Cl. ......... 604/372; 604/368; 423/267; 521/57; 427/2.3; 427/384

(58) Field of Classification Search ............... 604/367, 604/368, 370, 372; 423/267; 521/57; 427/2.3, 427/384
See application file for complete search history.

(56) References Cited

U.S. PATENT DOCUMENTS

| | | | |
|---|---|---|---|
| 3,656,996 A | 4/1972 | Van Paesschen et al. ..... 428/336 |
| 4,286,082 A | 8/1981 | Tsubakimoto et al. |
| 4,362,737 A | 12/1982 | Schafer et al. ............. 514/120 |
| 4,640,810 A | 2/1987 | Laursen et al. |
| 4,666,983 A | 5/1987 | Tsubakimoto et al. |
| 4,734,478 A | 3/1988 | Tsubakimoto et al. ....... 527/300 |
| 4,771,105 A | 9/1988 | Shirai et al. |
| 4,835,020 A | 5/1989 | Itoh et al. |
| 5,321,098 A | 6/1994 | Lal |
| 5,380,808 A | 1/1995 | Sumiya et al. |
| 5,409,771 A | 4/1995 | Dahmen et al. |
| 5,633,316 A | 5/1997 | Gartner et al. ............ 525/54.32 |
| 5,669,894 A | 9/1997 | Goldman et al. |
| 5,728,742 A | 3/1998 | Staples et al. ................... 521/57 |
| 5,763,067 A | 6/1998 | Brueggemann et al. |
| 5,840,321 A | 11/1998 | Engelhardt et al. |
| 5,945,495 A | 8/1999 | Daniel et al. |
| 5,994,440 A | 11/1999 | Staples et al. |
| 6,031,147 A | 2/2000 | Gross |
| 6,033,769 A | 3/2000 | Brueggemann et al. |
| 6,103,358 A | 8/2000 | Brueggemann et al. |
| 6,124,391 A | 9/2000 | Sun et al. |
| 6,146,570 A | 11/2000 | Stern |
| 6,156,024 A | 12/2000 | Schulte et al. ........... 604/385.28 |
| 6,291,636 B1 | 9/2001 | Miyake et al. |
| 6,675,702 B1 | 1/2004 | Maksimow |
| 2004/0071966 A1 | 4/2004 | Inger et al. |
| 2005/0020780 A1 | 1/2005 | Inger et al. |

FOREIGN PATENT DOCUMENTS

| | | |
|---|---|---|
| CA | 2 316 342 A1 | 6/2000 |
| DE | 40 20 780 C1 | 6/1990 |
| DE | 40 20 780 C1 | 8/1991 |
| DE | 44 18 319 A1 | 5/1994 |
| DE | 195 05 709 A1 | 2/1995 |
| DE | 196 01 763 A1 | 1/1996 |
| DE | 196 01 763 A1 | 7/1997 |
| DE | 197 50 890 A1 | 11/1997 |
| DE | 198 01 933 A1 | 1/1998 |
| DE | 197 50 890 A1 | 5/1999 |
| DE | 198 01 933 A1 | 7/1999 |
| DE | 100 16 041 A1 | 3/2000 |
| DE | 100 16 041 A1 | 10/2001 |
| EP | 0 388 120 A1 | 9/1990 |
| EP | 0 467 073 A1 | 1/1992 |
| EP | 0 509 708 A1 | 10/1992 |
| EP | 0 755 964 A2 | 7/1996 |
| EP | 0 755 964 | 1/1997 |
| EP | 0 850 615 | 7/1998 |
| EP | 0 850 615 A1 | 7/1998 |
| JP | S63270741 A | 11/1988 |
| JP | H04-175319 A | 6/1992 |
| JP | H11-292919 A | 10/1999 |
| JP | 2001-213914 A | 8/2001 |
| WO | WO 99/47249 | 9/1999 |
| WO | WO 99/49905 | 10/1999 |
| WO | WO 00/10619 | 3/2000 |

*Primary Examiner* — Lynne Anderson
(74) *Attorney, Agent, or Firm* — Smith Moore Leatherwood LLP; Philip P. McCann

(57) ABSTRACT

The present invention concerns highly swellable absorption mediums with a reduced caking tendency at high humidity and/or high temperatures, wherein a swellable polymer is coated with a non-ionic, nitrogen-containing surfactant and optionally a Lewis acid and then reacted by heating.

14 Claims, No Drawings

HIGHLY SWELLABLE ABSORPTION MEDIUM WITH REDUCED CAKING TENDENCY

This application is a divisional of U.S. Application Ser. No. 10/424,459, filed on Apr. 25, 2003, now pending, which is a continuation application of International Application No. PCT/EP2001/012315 filed Oct. 25, 2001, which claims priority to German Application No. DE 100 52 966.6 filed October 25, 2000, the disclosures of which are expressly incorporated herein by reference.

BACKGROUND OF THE INVENTION

The present invention relates to highly swellable absorption mediums having a reduced caking tendency in a moist environment and/or at high temperatures. The present invention also relates to the production and application of this absorption medium in hygiene articles and in technical fields.

Polymers that absorb aqueous fluids, termed superabsorbers, are known from a large number of publications. They are modified natural polymers and partially or totally synthetic polymers. Totally synthetic polymers are usually produced by radical polymerization of different hydrophilic monomers in aqueous solution using a variety of methods. In general, cross-linking agents are polymerized as well so that the polymer is no longer water-soluble but only water swellable. Polymers based, for example, on (meth)acrylic acids can be used as superabsorbers and are partially in the neutralized form as the alkali salt.

Superabsorbent polymers are usually used in the form of granulates as absorbing components in many hygiene articles such as diapers, feminine pads or absorbent dressings. Producing such articles requires exact proportions to be used that can only be guaranteed by constant conveying in the production plant. The highly hygroscopic nature of superabsorbent polymers causes problems at constant conveying speeds. This hygroscopic nature results in caking of the polymer particles, in particular when the humidity is relatively high and/or when the temperature is high. Agglomerated superabsorbers cannot be dosed precisely and stick to the walls of the production plant, resulting in increased cleaning costs. Thus, there have been many attempts in the past to develop superabsorbent polymers with a reduced caking tendency.

Many known processes reduce the hygroscopic nature by adding finely divided inorganic powder to the surface of the polymer particles. European patent EP 0 388 120 A describes the surface treatment of polymers with silicon dioxide powder with an average particle size of 0.1 to 30 μm.

U.S. Pat. No. 4,734,478 discloses polymers to which, after polymerization, a mixture of a polyalcohol and a hydrophilic organic solvent is added followed by heat treatment at >90° C. Subsequently, the surface cross-linked polymers are treated with 0.01% to 10% by weight of silica dust with a particle diameter of less than 10 μm. Such polymers are stated to have a high water uptake capacity as well as a reduced caking tendency.

U.S. Pat. No. 4,286,082 discloses processes for the production of water absorbing resins, in which at least one water-soluble, surface active reagent is added to the monomer solution and the polymer obtained is heat treated at a temperature of 100° C. to 230° C. The surface active reagents are preferably nonionic surfactants with an HLB of 7 to 20. To reduce the caking tendency of such polymers, the polymers are mixed with ultramicroscopic silica.

Since the dust content of such polymers is increased by treating with an inorganic powder, problems with dust arise, in particular when under mechanical stress such as the friction resulting from pneumatic conveying. Such a release of dust is preferably avoided for health reasons, so such polymers are more difficult to manipulate during production and use.

Attempts to produce polymers with a low dust content are described in U.S. Pat. No. 5,994,440. Such polymers are obtained by coating the surface of water-absorbent, cross-linked polymers with hydrophilic organic compounds that do not penetrate into the internal structure of the polymer. Suitable organic compounds are aliphatic polyols with a molecular weight of more than 200 g/mol. The surface coating causes the polymer dust to adhere to the polymer particles or to the wall of the storage container so that dust can be avoided. The loose dust portion of such a polymer is stated to be ≦2.5 ppm, with dust particles with a diameter of ≦10 μm being counted.

In another series of known processes, the surface of the absorbent particles is treated with hydrophobic agents to reduce the hygroscopic nature. Thus, EP 0 755 964 A2 describes highly swellable hydrogels the surface of which is coated with wax. Any wax with no reactive groups that can react with the carboxyl groups of the polymer surface can be used. Preferably, waxes with a melting point range of 30° C. to 180° C. are used.

EP 0 509 708 A1 discloses polymers obtained by surface cross-linking with polyhydroxy compounds and by coating the surface with surfactants with an HLB between 3 and 10. The polyhydroxy compounds can be any compound that has at least two hydroxyl groups and that can react with the carboxyl groups on the polymer particles. Preferred polyhydroxy compounds include polyglycols or lower glycol derivatives. Particular surfactants that can be used are sorbitan fatty acid esters, ethoxylated sorbitan fatty acid esters, glycerin or polyglycerin fatty acid esters or modified surface active polyesters.

A disadvantage of that process for surface coating polymers with hydrophobic substances is that the hydrophilic nature of the polymer surface is reduced, resulting in reduced liquid uptake rates.

U.S. Pat. No. 5,728,742 A discloses a non caking, non dusty composition obtained by treating water absorbing, lightly cross-linked polymers with an anti-caking agent and a hydrophilic de-dusting agent. Such dedusting agents are either polyols with a molecular weight of more than 200 g/mol or polyalkylene glycols with a molecular weight of 400 to 6000 g/mol. The anti-caking agents are cationic surfactants, for example quaternary ammonium or phosphonium salts.

DETAILED DESCRIPTION OF THE INVENTION

The aim of the present invention is to provide superabsorbent polymers that have a reduced caking tendency compared with absorption mediums that are known from the prior art, in particular in a moist environment such as high humidity and/or high temperatures, with at least equivalent properties, in particular at least an unchanged water uptake capacity, retention and uptake rate for water or aqueous fluids, in particular body fluids.

The present invention provides a highly swellable absorption medium with a reduced caking tendency in a moist environment and/or at high temperatures based on the following components:

I a water- or aqueous fluid-absorbing natural polymer modified with acid groups or a water-insoluble, optionally surface cross-linked, water- or aqueous fluid-absorbing cross-linked polymer based on polymerized monomers containing at least partially neutralized acid groups, which is treated with:

II at least one coating agent selected from the group formed by nitrogen-containing, non-ionic surfactants; and whereby the mixture formed from components I and II has been heat treated.

Preferably, the surfactant in the absorption medium of the invention is at least one compound with general formula I:

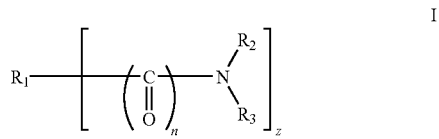

in which $R_1$ is a z-substituted aliphatic residue, preferably a z-substituted, saturated or unsaturated, linear or branched aliphatic $C_1$ to $C_{30}$ hydrocarbon residue, more preferably $C_8$ to $C_{22}$, which optionally carries aryl residues, preferably a phenyl residue, a z-substituted benzene residue, optionally condensed with five or six-membered rings optionally containing heteroatoms such as oxygen, phosphorus or nitrogen;

$R_2$ is a hydrogen; or an aliphatic residue, preferably a saturated or unsaturated, linear or branched $C_2$ to $C_{24}$ hydrocarbon residue, preferably $C_8$ to $C_{22}$;

a hydroxyalkylene residue, the hydroxyl group of said hydroxyalkylen residue is preferably an end group and/or optionally alkoxylated with 1 to 50, preferably 1 to 20, more particularly with 1 to 10 alkylene oxide units, preferably ethylene and/or propylene oxide units, and/or said hydroxyl group is optionally esterified with a carbon acid, preferably a $C_1$- to $C_8$-carbon acid, and the alkylene group of said hydroxyalkylen residue is a $C_1$- to $C_8$-, preferably $C_1$- to $C_4$-hydrocarbon group, occurs in the alkylene residue, or a N,N-dihydroxyalkylene-amino-alkylene residue with $C_1$-$C_4$ in each alkylene residue;

$R_3$, which may be identical or different, has the same meaning as $R_2$, provided that with amide compounds, at least one of residues $R_2$ or $R_3$ represents a hydroxyalkylene residue or an alkoxylated hydroxyalkylene residue or a corresponding esterified or alkoxylated or esterified and alkoxylated hydroxyalkylene residue with the definition given for $R_2$ above;

n is 0 or 1, preferably 1;

and z is a whole number from 1 to 4.

Preferably, component I is a powder. The particle size of this powder is preferably at least 20% by weight, preferably at least 50% by weight and more preferably at least 70% by weight in the range 150 to 1000 μm. Preferably again, less than 20% by weight, more preferably less than 10% by weight of the particles of the powder is less than 150 μm. The proportions given by weight in this paragraph all refer to the powder as a whole. The particle size can be determined using ERT-420.1-99.

It has surprisingly been discovered that coating water or aqueous fluid-absorbing polymers with at least one coating agent II of the invention possibly in combination with a Lewis acid III can produce absorption mediums with a significantly reduced caking tendency, while the other technical properties, in particular retention and absorption under load, are not affected. Further, the treated polymers have a reduced dust production.

The absorption medium of the invention exhibits at least one, preferably all of the following properties:

(a) no anti-caking after at least 3, preferably at least 6 and particularly preferably at least 24 h, most preferably in the range 3 to 30 hours, heat treatment being in accordance with the anti-caking tests described below;

(b) a retention of at least 20 g/g, preferably at least 25 g/g and particularly preferably at least 30 g/g, most preferably in the range 20 to 100 g/g;

(c) an absorption under load at a load of 0.9 psi ($AUL_{0.9psi}$) of at least 7 g/g, preferably at least 15 g/g and particular preferably at least 20 g/g, most preferably in the range 7 to 40 g/g.

Combinations of two or more of the above properties each produce preferred embodiments of the absorption medium of the invention; combinations ab, ac, be are preferred, with combinations ab and ac being particularly preferred.

Partially synthetic or totally synthetic polymers can be considered in addition to natural polymers as the water swellable hydrophilic polymers. Natural polymers modified with acidic groups, preferably carboxyl groups, that can be used are polysaccharides with carboxyl groups, preferably starches, celluloses, guar, for example carboxymethyl guar, xanthan gum, alginates, gum arabic, carboxymethylcellulose, carboxymethyl starches and mixtures of these polysaccharides. These polymers are water swellable and partially or totally water-insoluble.

Partially synthetic and totally synthetic polymers are preferably used, in particular anionic (meth)acrylic acid based polymers, which are in the partially neutralized form as alkali salts, in particular sodium and/or potassium salts. The degree of neutralisation of the acidic monomer components can vary, but is preferably in the range 25 mole % to 85 mole %. Homo- and co-polymers can be used that are obtained solely from acrylic acids and/or methacrylic acids, from such monomers together with one or more other monomers or alone from one or more other monomers, but, for example, they can also be grafted anionic polymers, for example based on (meth)acrylic acids, in the partially neutralized form as the alkali salt, for example graft polymers with polyvinyl alcohol, polysaccharides such as starches or cellulose or derivatives thereof or with polyalkylene oxides such as polyethylene oxides or polypropylene oxides.

Examples of monomers that can be used to produce the polymers in addition to (meth)acrylic acids are methyl, ethyl, and (poly)hydroxyalkylesters of (meth)acrylic acids, (meth)acrylamide, crotonic acid, maleic and fumaric acids, itaconic acid, 2-acrylamido-2-methylpropanesulphonic acid, vinylsulphonic acid and vinylphosphonic acids and the methyl, ethyl and poly(hydroxyalkyl)esters and amides of these acids, amino- and ammonium group-containing esters and amides of all said acids and water-soluble N-vinylamides, but also all other monomers usually employed as elemental units in the production of superabsorbent polymers can be contained in the polymer. The polymers are preferably cross-linked. Examples of suitable cross-linking compounds that can be used to produce the absorbent polymers and contain two or more reactive groups are polyglycidyl compounds such as polyglycidyl ether, methylene bis(meth)acrylamide, bis-acrylamido acetic acid, esters of unsaturated acids with polyols or alkoxylated polyols, for example ethylene glycol di(meth)acrylate or trimethylolpropane tri(meth)acrylate or allyl compounds, such as allyl(meth)acrylate, polyallyl esters, tetra-allyloxyethane, triallylamine, tetra-allylethylenediamine or allylesters of phosphoric acid as well as vinyl phosphonic acid derivatives or mixtures thereof. The proportion of cross-linking agents added during production of the absorbent polymer is preferably 0.01% to 20% by weight, more preferably 0.1% to 3% by weight with respect to the total monomer quantity.

Polymer production is carried out using known methods such as that described in German patent DE-C1-40 20 780 and which is hereby incorporated by reference and constitutes part of the disclosure. Preferably, the polymer is produced by polymerization in an aqueous solution using the gel polymerization process.

The polymer powder obtained by disintegrating, drying and grinding of the polymer gel can then undergo surface cross-linking.

Prior to surface cross-linking, the polymer is preferably dried, ground and screened to obtain the desired grain size fraction, then the surface cross-linking reaction is carried out. In some cases, however, it is pertinent to add the surface cross-linking agent before drying the polymer gel or before disintegrating the partially or essentially dry polymer. A surface cross-linking step that can be carried out in accordance with the invention has been described in U.S. Pat. No. 4,666,983 and DE-C-40 20 780. These documents are hereby incorporated by reference and thus constitute part of the disclosure. Preferably, the surface cross-linking agent is often added in the form of a solution in water, an organic solvent or a mixture thereof, in particular when small amounts of surface cross-linking agent are used. Examples of suitable mixing machines for adding the surface cross-linking agents are a Patterson-Kelley mixer, a DRAIS turbulence mixer, a Lödige mixer, a Ruberg mixer, a worm mixer, a pan mixer and a fluidised bed mixer, also continuous vertical mixers in which the powder is mixed at a high frequency using rotating knives (Schugi mixer). After the surface cross-linking agent has been mixed with the polymer, it is heated to temperatures of 60° C. to 250° C., preferably 135° C. to 200° C. and particularly preferably 150° C. to 185° C. to carry out the surface cross-linking reaction. The heating period must be limited so that the properties of the polymer are not affected by the heat treatment.

Preferred post cross-linking agents for surface cross-linking of the polymers are organic cross-linking agents, i.e., compounds that react with the surface COOH groups of the polymers, such as alkylene carbonates, for example 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one or 1,3-dioxepan-1-one. Particularly preferred compounds are 1,3-dioxolan-2-one and 4-methyl-1,3-dioxolan-2-one.

Further, the following compounds can be used as surface cross-linking agents: polyhydroxy compounds, for example ethyleneglycol, propyleneglycol, diethyleneglycol, dipropyleneglycol, triethyleneglycol, tetraethyleneglycol, tetrapropyleneglycol, polyethyleneglycol, polypropyleneglycol, 1,3-propanediol, glycerine, polyglycerine, 1,4-butanediol, 1,5-pentanediol, 1,6-hexanediol, trimethylolpropane, pentaerythritol or sorbitol; amino alcohols such as diethanolamine, triethanolamine. Further organic surface cross-linking agents that are not preferred on the grounds of their toxicity and so have to be severely limited in their use are: polyepoxides such as ethyleneglycol diglycidylether, polyethyleneglycol diglycidylether, glycerolpolyglycidylether polyglycerol polyglycidylether, propyleneglycol diglycidylether, polypropyleneglycol diglycidylether, glycidol; polyisocyanates such as 2,4-toluenediisocyanate and hexamethylenediisocyanate; halogenated epoxides such as epichlor- and epibromhydrin and α-methyl-epichlorhydrin; polyamine compounds such as ethylenediamine, diethylenetriamine, triethylenetetramine, polyallylamine or polyethyleneimine. Additional surface cross-linking agents that can be used are polyoxazolin compounds such as 1,2-ethylenebisoxazolin. The organic surface cross-linking agent is preferably used in amount of 0.01% to 5% by weight, more preferably 0.1% to 2.5% by weight and particularly preferably from 0.1% to 1% by weight, with respect to the polymer.

Non-ionic, nitrogen-containing surfactants can be used as coating agent II, preferably compounds with general formula I. However, a mixture of at least two compounds with this formula can also be used. Preferably, coating agent II is based on a fatty acid such as caprylic acid, caprinic acid, lauric acid, myristic acid, palmitic acid, palmitoleic acid, magaric acid, stearic acid, oleic acid, linoleic acid, linolenic acid, arachic acid, or eurecasic acid.

In particular, coating agent II is a fatty acid alkanolamide, the corresponding ethoxylated and/or propoxylated compounds, the esterified compounds; or fatty acid amines, the corresponding ethoxylated and/or propoxylated compounds, which can also be esterified. These include lauric acid monoethanolamide, coconut acid monoethanolamide, stearic acid monoethanolamide, ricinic acid monoethanolamide, undecylenic acid monoethanolamide, lauric acid diethanolamide, coconut acid diethanolamide, soya acid diethanolamide, linoleic acid diethanolamide, laurylmyristinic acid diethanolamide, oleic acid diethanolamide, lauric acid isopropanolamide, coconut acid isopropanolamide, oleic acid isopropanolamide, undecylenic acid polydiethanolamide, coconut acid polydiethanolamide, stearylamine, stearyl propylenediamine, coconut acid amine, laurylamine, oleylamine, stearylamine, tallow acid amine, the ethoxylates and/or propoxylates of said compounds, which may contain 1 to 50, preferably 1 to 20 alkylene oxide units, also the esters of said compounds, such as coconut acid monoethanolamide acetate. Mixtures of said compounds can also be used.

Coating agents II are preferably employed in a concentration of 50 to 50000 ppm, particular preferably 100 to 5000 ppm, still more preferably 300 to 3000 ppm with respect to component I.

In a particular embodiment of the present invention, at least one Lewis acid is added as coating agent III to the polymers in addition to at least one coating agent II. In accordance with the invention, electron pair acceptors can be employed as the Lewis acid.

The compounds that can be used as Lewis acid III or coating agent III in the absorption medium of the invention are inorganic acids, water-soluble, saturated or unsaturated organic acids, water-soluble hydrocarbon acids or water-soluble acid salts.

The Lewis acids are preferably inorganic acids such as hydrogen halides, oxyhalogen acids, sulphur or selenium oxyacids, nitrogen or phosphorus oxyacids, organic acids such as water-soluble saturated or unsaturated organic acids, and/or water-soluble acid salts such as water-soluble bromides, chlorides, nitrates, sulphates, phosphates or salts of organic acids such as the acetate, formate, oxalate and lactate of the metals Al, Fe, Zn, Sb, As, Sn, Cu, Mg, Ca, Cr, Ga, V, Ti, Bi, Tl, In, Mn, Ni, Co, Be und zirconium.

Preferably, the inorganic acids are hydrochloric acid, perchloric acid, bromic acid, hydrobromic acid, sulphuric acid, sulphur-containing acids, selenic acid, nitric acid, phosphonic acid or phosphorus-containing acids; the organic water-soluble acids are preferably carbonic acid, hydrocarbon acids, sulphonic acids or phosphonic acids or the corresponding amino acids, for example acrylic acid, methacrylic acid, formic acid, acetic acid, propionic acid, butyric acid, oxalic acid, malonic acid, succinic acid, lactic acid, maleic acid, fumaric acid, benzoic acid, phthalic acid, salicylic acid, tartaric acid, citric acid, p-, m- und o-toluenesulphonic acid, benzenesulphonic acid, aminomethanesulphonic acid, aminomethanephosphonic acid; and the acid salts are aluminium salts, alums and their various hydrates such as $AlCl_3 \times 6H_2O$, $NaAl(SO_4)_2 \times 12H_2O$, $KAl(SO_4)_2 \times 12H_2O$ or $Al_2(SO_4)_3 \times 14\text{-}18H_2O$, zinc salts and their hydrates such as $ZnCl_2$, $ZnSO_4 \times 1\text{-}7H_2O$ and $Zn(CH_3COO)_2 \times 2H_2O$, iron salts and their hydrates such as $NaFe(SO_4)_2 \times 12H_2O$, $KFe(SO_4)_2 \times 12H_2O$ and $Fe_2(SO_4)_3 \times nH_2O$, Mg-salts such as $MgCl_2$ or $MgSO_4$, double salts, also mixtures of the salts and mixtures of the inorganic and/or organic acids and mixtures of the salts with the inorganic and/or organic acids.

Particularly preferred compounds are: for the inorganic acids, sulphuric acid or phosphoric acid; for the acid salts: $AlCl_3 \times 6H_2O$, $Al_2(SO_4)_3 \times 14\text{-}18H_2O$, $ZnCl_2$, $ZnSO_4 \times 1\text{-}7H_2O$, $Zn(CH_3COO)_2 \times 2H_2O$, $MgSO_4$, $MgCl_2$; and for the organic acids, acetic acid, oxalic acid, lactic acid, citric acid and tartaric acid.

Particularly preferably, the Lewis acid is sulphuric acid, phosphoric acid, formic acid, acetic acid, citric acid or p-toluenesulphonic acid, an aluminium salt or alum and/or their various hydrates, zinc salts and/or hydrates thereof, magnesium salts and/or hydrates thereof and/or double salts.

In accordance with the invention, at least one Lewis acid is used. However, a mixture of at least two of the cited Lewis acids can be used.

The total amount of coating agents II and III is 100 to 50000 ppm, preferably 300 to 25000 ppm, more particularly 500 to 13000 ppm with respect to component I.

Coating agent II can be added with Lewis acid III or before or after carrying out the surface cross-linking step or simultaneously with the cross-linking agent, and then undergo the heat treatment with polymer I. Alternatively, when a combination of coating agent II with Lewis acid III is used, the two compounds can be added separately, preferably as aqueous solutions, or they can be added simultaneously to polymer I, optionally together with the cross-linking agent, preferably as an aqueous solution. Preferably, coating agent II, optionally in combination with Lewis acid III, is added simultaneously with the cross-linking agent and the coated polymer then undergoes heat treatment, thus dispensing with an additional process step. Particularly preferably, component I is coated with an aqueous solution of coating agent II and III and then reacted. Still more preferably, coating agent II is a fatty acid alkanolamide or a fatty acid amine with formula I, which may be alkoxylated and/or esterified.

Suitable solvents are water or polar, water-miscible organic solvents such as acetone, methanol, ethanol or 2-propanol or mixtures thereof, preferably water. The term "aqueous solution" as used in the context of the invention means, when referring to solvent components, that they can also contain organic solvents in addition to water. The concentration of the optional cross-linking agent in the coating solution can vary between wide limits and is primarily in the range 1% to 80% by weight, preferably in the range 1% to 60% by weight, particularly preferably in the range 10% to 50% by weight. The concentration of coating agent II or optional Lewis acid III in the solution can also vary between wide limits, preferably in the range 0.5% to 80% by weight, preferably in the range 0.5% to 60% by weight, particularly preferably in the range 0.5% to 60% by weight and particularly preferably in the range 0.5% to 30% by weight. The preferred solvent for the optional organic cross-linking agent and coating agent II and optional Lewis acid III is water, preferably in an amount of 0.5% to 10% by weight, particularly preferably 0.5% to 5% by weight and still more preferably 0.5% to 4% by weight with respect to polymer I.

To obtain the desired properties, the coating solution(s) must be evenly distributed on the absorbent polymer. To this end, the components are thoroughly and homogeneously mixed in suitable mixers, such as fluidised bed mixers, pan mixers, roller mixers or twin screw mixers.

It is also possible to coat the polymers during production of the polymer, preferably at the final stage of polymerization. To this end, reverse suspension polymerization is suitable.

Heat treatment of component I coated with coating agent II or a corresponding coating solution is preferably carried out at temperatures of 100° C. to 250° C., particularly preferably 150° C. to 230° C., more particularly preferably 150° C. to 210° C., to cause component I to react with the coating agent.

If coating agent II and III or the corresponding coating solution is used, heat treatment is preferably carried out at a temperature of 40° C. to 250° C., particularly preferably 100° C. to 230° C., more particularly preferably 130° C. to 210° C., to cause component to react with the coating agent.

Preferably, coating agent II is added to the absorbent polymer in combination with a Lewis acid III before, after or simultaneously with the cross-linking agent prior to heat treatment, as in this case the temperature and duration of the heat treatment is lower and shorter than when treating the absorbent polymer with coating agent II without Lewis acid III.

The particle size of the powder to be coated is preferably in the range 50 to 5000 μm, particularly preferably in the range 50 to 1000 μm and more particularly preferably in the range 50 to 850 μm. The particle size is determined using known screening methods.

The heat treatment period is also dependent on the selected temperature. It should be noted in this regard that the higher the temperature, the shorter the period. The treatment time and temperature are selected so that the treated polymer has a reduced caking tendency, i.e., it passes the anti-caking test ($\geq 3$ hours), retaining or improving the retention, absorption under load and uptake rate for water or aqueous fluids, in particular body fluids, compared with superabsorbent polymers that are not in accordance with the invention. For polymers based on partially neutralized and cross-linked poly (meth)acrylic acids, this means a retention of $\geq 20$ g/g and an $AUL_{0.9}$ of $\geq 19$ g/g using the methods described below.

The invention also concerns absorbent agent produced by the process of the invention.

The polymers treated in accordance with the invention are easy to manipulate, for example easy to convey and dose.

The polymers of the invention or absorbent agents are preferably used in absorbent hygiene products such as diapers, incontinence products for adults and feminine pads.

Absorbent hygiene products usually have a general construction constituted by a fluid-permeable cover facing the body, a fluid-absorbing absorbent layer and an essentially fluid impermeable, outer layer facing away from the body. Optionally, they may have further means for rapid uptake and distribution of body fluids to the absorbent core. These constructions are often, but not necessarily between the fluid-permeable cover facing the body and the fluid-absorbing absorbent core.

The fluid-permeable cover usually consists of a nonwoven, fibrous fabric or a different porous construction.

Examples of materials for this cover are synthetic polymers such as polyvinyl chloride or fluoride, polytetrafluorethylene (PTFE), polyvinylalcohols and their derivatives, polyacrylates, polyamides, polyesters, polyurethanes, polystyrene, polysiloxane or polyolefins (for example polyethylene (PE) or polypropylene (PP)), also natural fibrous materials and combinations of the above materials as mixed materials or composites or copolymers.

The fluid permeable cover is hydrophilic in nature. It can also consist of a combination of hydrophilic and hydrophobic components. Preferably, the fluid-permeable cover has a hydrophilic framework so that body fluids can trickle quickly through into the fluid-absorbing absorbent layer, however partially hydrophobic covers are also used.

Fluid-absorbing absorbent layer.

The fluid-absorbing absorbent layer contains the superabsorbent powdered or granulated polymer of the invention and further components, for example fibrous materials, foamed materials, film-forming materials or porous materials as well as combinations of two or more of such materials. Each material can be natural or synthetic in origin or can be produced by chemical or physical modification of natural materials. The materials can be hydrophilic or hydrophobic, preferably hydrophilic. This is particularly the case for compositions that efficiently take up exuded body fluids and transport the body fluid to a location in the absorbent core that is at a distance from the entry point.

Suitable fibrous materials are cellulose fibres, modified cellulose fibres (for example stiffened cellulose fibres), polyester fibres (for example Dacron), hydrophilic nylon or hydrophilised hydrophobic fibres, such as polyolefins (PE, PP) hydrophilised with surfactants, polyesters, polyacrylates, polyamides, polystyrene, polyurethanes and the like.

Preferably, cellulose fibres and modified cellulose fibres are used. Combinations of cellulose fibres and/or modified cellulose fibres with synthetic fibres such as PE/PP composite materials, termed bi-component fibres, such as those used for thremobonding of air laid materials, or other materials can also be used.

The fibrous materials can be in different forms, for example loose from an air stream or as an aqueous phase or deposited cellulose fibres, as a nonwoven fabric or as a tissue. Combinations of different forms are possible.

Optionally, in addition to the superabsorber of the invention, other powdered substances can be used, for example odour-binding substances such as cyclodextrin, zeolites, inorganic or organic salts and the like.

The porous materials and foamed materials can, for example, be polymer foams such as those described in DE 44 18 319 A1 and DE 195 05 709 A1, hereby incorporated by reference and considered to constitute part of the disclosure.

Thermoplastic fibres (for example bi-component fibres of polyolefins, polyolefin granulates, latex dispersions or hot melt adhesives) can be used to stabilise the fluid-absorbing absorbent layer mechanically. Optionally, one or more layers of tissue can be used for stabilisation.

The fluid-absorbing absorbent layer can be a single layer, or it can consist of a plurality of layers. Preferably, constructions are used that consist of hydrophilic fibres, preferably cellulose fibres, optionally a construction for rapid uptake and distribution of body fluids, such as chemically stiffened (modified) cellulose fibres or high loft fabric from hydrophilic or hydrophilised fibres, and superabsorbent polymers.

The superabsorbent polymer of the invention can be homogeneously distributed in the cellulose fibres or stiffened cellulose fibres, it can be layered between the cellulose fibres or stiffened cellulose fibres, or the concentration of superabsorbent polymer can be graduated within the cellulose fibres or stiffened cellulose fibres. The ratio of the total amount of superabsorbent polymer to the total amount of cellulose fibres or stiffened cellulose fibres in the absorbent core can be between 0 to 100 and 80 to 20, while in one embodiment, for example that with a gradient or layered structure, local concentrations of up to 100% by weight of polymer can be obtained. Such constructions with regions of high concentrations of absorbent polymer, where the proportion of superabsorber in certain regions is between 60% and 100% by weight, or between 90% and 100% by weight at its highest, each based on the total weight of the construction, are described, for example, in U.S. Pat. No. 5,669,894 A, hereby incorporated by reference and considered to constitute part of the disclosure.

Optionally, a plurality of different absorbent polymers differing, for example, in absorbing speed, permeability, storage capacity, absorption under load, grain size distribution or chemical composition, can be used at the same time. These different polymers can be mixed together in the absorbent pad or can be in different locations in the absorbent core. Such differentiated positioning can be along the thickness of the absorbent pad or along the length or breadth of the absorbent pad.

One or more of the layers of cellulose fibres or stiffened cellulose fibres containing superabsorbent polymers are contained in the absorbing absorbent layer. In a preferred embodiment, constructions of combinations of layers with homogeneous superabsorbing layers and additional layers are used.

Optionally, the cited structures can be supplemented by further layers of pure cellulose fibres or stiffened cellulose fibres on the side facing the body and/or facing away from the body.

The constructions described above can be repeated a plurality of times, by stacking two or more similar layers or by stacking two or more different constructions. The differences may be entirely constructive or may reside in the type of the materials used, such as the use of absorbent polymers with different properties or different cellulose types.

Optionally, the entire absorbent pad or individual layers of the absorbing absorbent layer can be separated from the other components with layers of tissue or they may be in direct contact with other layers or components.

As an example, the structure for rapid uptake and distribution of body fluids can be separated from the absorbing absorbent layer by tissue or they can be in direct contact with each other. If no separate construction for rapid uptake and distribution of body fluid exists between the absorbing absorbent layer and the fluid-permeable cover facing the body, but the effect of fluid distribution is to be obtained, for example by using a special fluid-permeable cover on the body side, the fluid-permeable cover facing the body can optionally be separated from the fluid-absorbing absorbent layer by a tissue.

Optionally, instead of tissue, a nonwoven fabric can be added to the fluid-absorbing absorbent layer. Both components result in the desired side effect of stabilising and fixing the absorbent core when moist.

Process for producing the fluid-absorbing absorbent layer.

Fibre-containing, superabsorber-containing, fluid distributing and storing layers can be generated by a plurality of processes.

Established conventional processes, summarised by the skilled person as drum forming with the assistance of shaping wheels, pockets and product shapes and suitable corresponding dosing apparatus for the raw materials, are supplemented by modern processes such as the air laid process (e.g. EP 850

615, cn. 4 line 39 to cn. 5 line 29, U.S. Pat. No. 4,640,810) with all types of dosing, deposition of fibres and fixing such as hydrogen bonding (e.g. DE 197 50 890, cn. 1 line 45 to cn. 3 line 50, thermo bonding, latex bonding (e.g. EP 850 615, cn. 8 line 33 to cn. 9 line 17 and hybrid bonding, the wet laid process (e.g. PCT WO 99/49905, cn. 4 line 14 to cn. 7 line 16), carding, melt blown, spun blown processes and similar processes for the production of superabsorber-containing nonwovens (as defined by EDANA, Brussels), also combinations of these processes with other normal methods for the production of the cited fluid storage means. The documents cited above are hereby incorporated by reference and should be considered to constitute part of the disclosure.

Further processes that can be considered are the production of laminates in the broadest sense and the production of extruded and co-extruded, wet and dry structures and postformed structures.

A combination of these processes with each other is also possible.

Constructions for rapid uptake and distribution of body fluids

A construction for rapid uptake and distribution of body fluids consists, for example, of chemically stiffened (modified) cellulose fibres or high loft fabrics of hydrophilic or hydrophilised fibres or a combination of the two.

Chemically stiffened, modified cellulose fibres can, for example, be produced from cellulose fibres, which are chemically transformed by cross-linking agents such as $C_2$-$C_8$ dialdehydes, $C_2$-$C_8$ monoaldehydes with an additional acid function, or $C_2$-$C_9$ polycarbon acids. Particular examples are: glutaraldehyde, glyoxal, glyoxalic acid or citric acid. Cationically modified starches or polyamide-epichlorhydrin resins (for example KYMENE 557H, Hercules Inc., Wilmington, Del.) are also known. Cross-linking produces a twisted, crumpled structure that is stable, which advantageously affects the rate of fluid uptake.

Weight per unit area and density of absorbent articles

The absorbent hygiene products can vary widely in weight per unit area and thickness and thus in density. Typically, the density of the absorbent core is in the range 0.08 to 0.25 g/cm$^3$. The weight per unit area is between 10 and 1000 g/m$^2$, and preferably the weight per unit area is between 100 and 600 g/m$^2$ (see also U.S. Pat. No. 5,669,894, hereby incorporated by reference and considered to constitute part of the disclosure). The density normally varies over the length of the absorbent core. This is as a result of predetermined dosing of the cellulose fibre or stiffened cellulose fibre or the amount of the superabsorbent polymer, as in preferred embodiments, these components are more concentrated in the frontal area of the absorbent disposable articles.

This deliberate increase in the concentration of absorbent material in particular regions of the absorbent core can be achieved in other ways, for example by producing an appropriately dimensioned flat form using an air laid or wet laid process consisting of hydrophilic cellulose fibres, optionally from stiffened cellulose fibres, optionally from synthetic fibres (for example polyolefins) and superabsorbent polymers and then folding it back or stacking Test Methods Unless otherwise indicated, the following tests are carried out using polymers with a particle size of 300 to 600 µm (determined using the screen method).

Anti-Caking Test:

5 g±0.1 of polymer with a particle size of 150 to 180 µm is weighed into an aluminium weighing boat (57 mm) and distributed homogeneously over the entire boat. The boat is weighed. Then the boat is placed in a heated cabinet at a temperature of 35° C. with a relative humidity of 80% for 3, 6 or 24 h. Then the boat is weighed again. A further boat is weighed and a sieve with a mesh of 1.5 mm is placed over it. The sample is tipped onto the sieve. After tapping lightly on the sieve a number of times, the weight of the product that has fallen through the sieve is measured.

The test is considered to have been passed when more than 90% by weight of the product falls through the sieve. The water uptake of the product is also determined.

Method for Measuring Surface Tension:

Measurement of Surface Tension of Aqueous Solutions Using a Traube-Gerhardt Stalagmometer.

A stalagmometer is a type of volumetric pipette that empties into a very carefully produced drip surface. On this polished surface, droplets form one after the other, the size of which is dependent on the surface tension of the product under consideration. The higher the surface tension, the larger the droplets, and vice versa. The volume of the pipette is calibrated with circular marks. Since the volume is constant and the droplet size is dependent on the surface tension, the number of droplets is a direct measure of the surface tension. The value that is measured, therefore, is compared with the number of droplets of pure water, the surface tension of which is known.

150 g of 0.9% NaCl solution is placed in a 250 ml beaker and stirred with a magnetic stirrer (200 rpm). 1 g of the test polymer is slowly scattered in the spout formed by the 0.9% NaCl solution. When scattering is complete, the solution is stirred for 3 minutes. It is then allowed to stand for 15 minutes.

The test solution is drawn up to well beyond the upper pipette volume mark using a pipette bulb. The number of droplets between the upper and lower mark are counted. Each solution is tested twice.

Calculation of surface tension in mN/m=Number of droplets of pure water×72.75*/test sample droplet number*(surface tension of water in mN/m).

Measuring the surface tension establishes how much coating agent may be released into an aqueous environment. In other words, this measurement establishes how well the coating agent is bonded to the polymer. If the surface tension is reduced by the coating, then the problem of re-wetting can occur. Re-wetting causes fluids, for example urine, that have already been absorbed to be released, for example, by pressure on the 0swollen gel, meaning that the hygiene article is not comfortable for the wearer.

Retention:

The retention is obtained using the teabag method and the average of three measurements is taken. About 200 mg of polymer is sealed in a teabag and soaked in 0.9% NaCl solution for 30 minutes. Then the teabag is centrifuged in a centrifuge (23 cm diameter, 1400 rpm) for 3 minutes and then weighed. A teabag with no absorbent polymer is run at the same time as a reference.

Retention [g/g]=endothermic weight−reference weight/starting weight

Fluid Uptake Under 0.9 psi Load, AUL:

0.16 g of polymer is accurately weighed into a Plexiglas cylinder with an internal diameter of 25.4 mm fitted with a 400 mesh nylon sieve base. The layer of polymer evenly distributed on the sieve base is covered with a 26.1 mm diameter Teflon disk and weighed down with a cylindrical piston weighing 332.4 g. The Teflon disk and piston together constitute a load of 63 g/cm$^2$, or 0.9 psi. The weighed cylinder is then placed on a glass filter plate in a dish with 0.9% NaCl solution the depth of which exactly corresponds to the depth of the filter plate. After the cylinder assembly has been left for 1 hour to allow the 0.9% NaCl solution to be absorbed, the filter paper is patted free of excess test solution and then re-weighed and the AUL is calculated as follows:

AUL=final weight (cylinder assembly+swollen polymer)−start weight (cylinder assembly+non swollen polymer)/polymer start weight

EXAMPLES

The invention will now be illustrated by examples. The examples are given purely by way of illustration and in no way limit the scope of the invention.

The following abbreviations are used:
ABAH 2.2'-azo-bis-amidinopropane-dihydrochloride
AIBN 2.2'-azo-bis-2-methylpropionitrile
AMPS 2-acrylamido-2-methylpropanesulphonic acid
BO 2-butyl-octanol
EO ethylene oxide (1,2-epoxyethane)
IHD isohexadecane
ITDA isotridecylalcohol
ITS isotridecylstearate
DN degree of neutralisation, mole-%
OABOE oleic acid butyloctyl ester
ROSME rapeseed oil acid methyl ester
TAMAC triallylmethylammonium chloride Comparative Example 1

U.S. Pat. No. 5,728,742

1000 ppm of Ethoquad 0/12 dissolved in 3 g of isopropanol was added, using a syringe, stirring with a mixer, to 50 g of powdered polyacrylate that had been 70% neutralized and surface cross-linked (Favor SXM 880®, available from Stockhausen GmbH & Co. KG), with a retention of 32 g/g in 0.9% NaCl-solution and a $AUL_{0.9\,psi}$ of 22.1 g/g. The polymer was rolled for 60 minutes on a roll bench at ambient temperature. The product did not pass the 3 h anti-caking test described above.
Ethoquad 0/12=oleylmethyldi(2-hydroxyethyl)ammonium chloride Comparative Example 2

U.S. Pat. No. 5,728,742

1000 ppm of Arquad 16-50 dissolved in 3 g of isopropanol was added, using a syringe, stirring with a mixer, to 50 g of powdered polyacrylate as described in comparative example 1 (Favor SXM 880®, available from Stockhausen GmbH & Co. KG). The polymer was rolled for 60 minutes on a roll bench at ambient temperature. The product did not pass the 3 h anti-caking test described above.
Arquad 16-50=Hexadecyltrimethylammonium Chloride
Production of Polymer Powders 1-5
Powder 1:
290 g of acrylic acid was divided into two equal portions. One portion was added to 458.5 g of $H_2O$. 0.85 g of polyethylene glycol −300-diacrylate and 1.5 g of allyloxypolyethylene glycol acrylic acid ester were dissolved in the second portion of acrylic acid and then added to the water. The solution was cooled to 10° C., then a total of 225.4 g of 50% sodium hydroxide was slowly added with cooling so that the temperature did not exceed 30° C. The solution was then flushed with nitrogen at 20° C. and then cooled again. When the start temperature of 4° C. had been reached, the initiator solutions (0.1 g of 2.2'-azobis-2-amidinopropane-dihydrochloride in 10 g $H_2O$, 1.0 g sodium peroxydisulphate in 10 g $H_2O$, 0.1 g 30% hydrogen peroxide solution in 1 g $H_2O$ and 0.015 g ascorbic acid in 2 g water) was added. After the final temperature of 102° C. had been reached, the gel that had formed was disintegrated and then dried for 90 minutes at 150° C. the dried polymer was coarsely crushed, ground and screened to a powder with a particle size of 150 to 850 µm.
Powder 2:
300 g of acrylic acid was divided into two equal portions. One portion was added to 429.1 g of $H_2O$. 0.36 g of triallylamine, 1.05 g of allyloxypolyethylene glycol acrylic acid ester and 12 g of methoxypolyethylene glycol (22EO) methacrylate were dissolved in the second portion of acrylic acid and then added to the water. The solution was cooled to 10° C. Then a total of 233.1 g of 50% sodium hydroxide was slowly added with cooling so that the temperature did not exceed 30° C. The solution was then flushed with nitrogen at 20° C. and then cooled again. When the start temperature of 4° C. had been reached, 0.9 g of sodium carbonate and the initiator solutions (0.1 g of 2.2"-azobis-2-amidinopropane-dihydrochloride in 10 g $H_2O$, 0.15 g of sodium peroxydisulphate in 10 g $H_2O$, 0.1 g of 30% hydrogen peroxide solution in 1 g $H_2O$ and 0.01 g ascorbic acid in 2 g water) were added. After the final temperature of 104° C. had been reached, the gel that had formed was disintegrated and then dried for 90 minutes at 150° C. The dried polymer was coarsely crushed, ground and screened to a powder with a particle size of 150 to 850 µm.
Powder 3:
was a non surface cross-linked polyacrylic acid (fabrication product of Favor SXM 880®), 70% neutralized and with a retention of 40 g/g in 0.9% NaCl solution and an AUL of 8.7 g/g.
Powder 4:
280 g of acrylic acid was divided into two equal portions. One portion was added to 517.04 g of $H_2O$. 0.28 g of triallylamine, 0.72 g of allyloxypolyethylene glycol acrylic acid ester and 7.51 g of methoxypolyethylene glycol (22EO) methacrylate were dissolved in the second portion of acrylic acid and then added to the water. The solution was cooled to 10° C. Then a total of 170.97 g of 50% sodium hydroxide was slowly added with cooling so that the temperature did not exceed 30° C. The solution was then flushed with nitrogen at 20° C. and then cooled again. When the start temperature of 4° C. had been reached, 0.9 g of sodium carbonate and the initiator solutions (0.1 g of 2.2"-azobis-2-amidinopropane-dihydrochloride in 10 g of $H_2O$, 1.0 g of sodium peroxydisulphate in 10 g $H_2O$, 0.07 g of 30% hydrogen peroxide solution in 1 g $H_2O$ and 0.01 g ascorbic acid in 2 g water) were added. After the final temperature of 102° C. had been reached, the gel that had formed was disintegrated and then dried for 90 minutes at 150° C. The dried polymer was coarsely crushed, ground and screened to a powder with a particle size of 150 to 850 µm.
Powder 5:
was the non surface cross-linked polyacrylic acid of comparative Example 1 with a retention of 32 g/g in 0.9% NaCl solution and an AUL of 22.1 g/g (Favor SXM 880®).

Example 1

A mixture of 0.015 g of Comperlan COD, 0.25 g of ethylene carbonate as a cross-linking agent, 1.0 g of $H_2O$ and 4.0 g of acetone was added to 50 g of powder 1, stirring with a mixer (Krups Dry Mix Type 7007) on its highest setting. The coated polymer was evenly poured into a photographic tank and dried for 30 minutes in a circulating air drying oven at 180° C. The retention, AUL value, surface tension and anti-caking tests were carried out as described above and the results are shown in Table 1.

Examples 2-17

Examples 2-17 were carried out as described for Example 1. The powder used, added compounds, the amounts of the compounds and the duration and temperature of the heat treatment are shown in Table I along with the corresponding retention, AUL, surface tension and the results of the anti-caking tests.

Comparative Example 3

A mixture of 0.05 g of Imbentin CMEA/045 in 1.0 g of $H_2O$ was added to 50 g of powder 5, stirring with a mixer (Krups Dry Mix Type 7007) on its highest setting; it was then stirred for a further 2 minutes. No heat treatment was carried out. The polymer did not pass the 3 h anti-caking test and had reduced pourability.

The polymer had a retention of 31.4 g/g and an AUL of 21.3 g/g.

Example 18

A mixture of 0.05 g of Imbertin CMEA/045 in 1.0 g of $H_2O$ was added to 50 g of powder 5, stirring with a mixer (Krups Dry Mix Type 7007) on its highest setting. It was then stirred for a further 2 minutes. The product was poured into a photographic tank and dried for 20 minutes in a circulating air drying oven at 180° C. The treated polymer passed the anti-caking test. Its retention, AUL and surface tension are shown in Table 1.

Example 19

A mixture of 0.05 g of Imbentin CMEA/045 in 1.0 g of $H_2O$ was added to 50 g of powder 5, stirring with a mixer (Krups Dry Mix Type 7007) on its highest setting. It was then stirred for a further 2 minutes. The product was poured into a photographic tank and dried for 15 minutes in a circulating air drying oven at 190° C. The treated polymer passed the anti-caking test. Its retention, AUL and surface tension are shown in Table 1.

TABLE 1

| Example | Powder | Anti-caking substance | Conc'n, wt % with respect to product | Temperature/ time [° C./t] | 3 h anti-caking test | Retention [g/g] | AUL 0.9 psi [g/g] | Surface tension [mN/m] |
|---|---|---|---|---|---|---|---|---|
|  | 1 | — |  | 180/30 | − | 31.5 | 17.7 |  |
| 1 | 1 | Comperlan COD | 0.015 | 180/30 | + | 31.5 | 17.6 | 72.5 |
| 2 | 1 | Comperlan LD | 0.06 | 180/30 | + | 32.8 | 17.4 | 72.5 |
|  | 2 | — |  | 180/30 | − | 34.8 | 23.5 | — |
| 3 | 2 | Marlazin L10 | 0.03 | 180/40 | + | 35.0 | 23.7 | 72.5 |
| 4 | 2 | Marlazin L10 | 0.10 | 180/40 | + | 34.9 | 23.8 | 72.5 |
| 5 | 2 | Serdox NXC 3 | 0.10 | 180/30 | + | 34.5 | 22.5 | 72.5 |
| 6 | 2 | Serdox NXC 6 | 0.10 | 180/40 | + | 35.0 | 21.0 | 72.5 |
| 7 | 2 | Serdox NXC 14 | 0.10 | 180/40 | + | 34.8 | 22.0 | 72.5 |
| 8 | 2 | Serdox NXC 6 | 0.05 | 180/40 | + | 35.2 | 22.3 | 72.5 |
|  | 3 | — |  | 190/25 | − | 32.4 | 21.2 | — |
| 9 | 3 | Serdox NXC 6 | 0.10 | 180/35 | + | 32.3 | 19.1 | 72.5 |
| 10 | 3 | Marlazin OL 20 | 0.10 | 180/35 | + | 32.3 | 20.3 | 72.5 |
| 11 | 3 | Marlazin L10 | 0.10 | 180/35 | + | 32.3 | 19.5 | 72.5 |
| 12 | 3 | Comperlan COD | 0.2 | 180/30 | + | 31.3 | 21.1 | 72.5 |
| 13 | 3 | Serdox NXC 6 | 0.1 | 180/30 | + | 31.7 | 21.2 | 72.5 |
| 14 | 3 | Imbentin CMEA/045 | 0.1 | 190/20 | + | 32.1 | 21.0 | 72.5 |
| 15 | 3 | Imbentin CMEA/045 | 0.2 | 190/20 | + | 32.0 | 20.8 | 72.5 |
|  | 4 | — |  | 170/25 | − | 30.5 | 21.0 | — |
| 16 | 4 | Stokomin S10 | 0.1 | 170/25 | + | 30.1 | 21.2 | 72.5 |
| 17 | 4 | Serdox NXC 3 | 0.1 | 170/25 | + | 30.9 | 20.4 | 72.5 |
|  | 5 | — |  |  |  | 32.0 | 22.1 |  |
| 18 | 5 | Imbentin CMEA/045 | 0.05 | 180/20 | + | 30.9 | 20.8 | 72.5 |

TABLE 1-continued

| Example | Powder | Anti-caking substance | Conc'n, wt % with respect to product | Temperature/ time [° C./t] | 3 h anti-caking test | Retention [g/g] | AUL 0.9 psi [g/g] | Surface tension [mN/m] |
|---|---|---|---|---|---|---|---|---|
| 19 | 5 | Imbentin CMEA/045 | 0.05 | 190/15 | + | 30.8 | 21.0 | 72.5 |

Stokomin S10 = Stearylamine, ethoxylated with 10 EO;
Comperlan COD = coconut acid diethanolamide (Henkel KGaA);
Comperlan LD = lauric acid diethanolamide (Henkel KGaA);
Comperlan 100 = coconut acid monoethanolamide (Henkel KGaA);
Marlazin L10 = laurylamine, ethoxylated with 10 EO (Contensio);
Marlazin OL 20 = oleylamine, ethoxylated with 20 EO (Contensio);
Serdox NXC 3 = Oleic acid monoethanolamide, ethoxylated with 3 EO (Condea);
Serdox NXC 6 = Oleic acid monoethanolamide, ethoxylated with 6 EO (Condea);
Serdox NXC 14 = Oleic acid monoethanolamide, ethoxylated with 14 EO (Condea);
Imbentin CMEA/045 = coconut acid monoethanolamide, ethoxylated with 4.5 EO
Comparative value for surface tension of water: σ = 72.5 mN/m
+: test passed
−: test failed

Comparative Example 4

0.5 g of ethylene carbonate, 2 g of water and 0.25 g of $Al_2(SO_4)_3 \times 18H_2O$ were mixed together and added using a syringe to 50 g of powder 3, stirring with a mixer (Krups Dry Mix Type 7007) on its highest setting. The product was poured into a photographic tank and dried for 50 minutes in a circulating air drying oven at 170° C.

The treated polymer failed the 3 h anti-caking test. Its retention, AUL and surface tension are shown in Table 2.

Example 20

Powder 3 was mixed with 0.7% by weight of ethylene carbonate, 1.8% by weight of water, 0.2% by weight of $Al_2(SO_4)_3 \times 14H_2O$ and 0.2% by weight of Imbentin CMEA/024 (Kolb AG) in a mixer (Krups Dry Mix Type 7007) on its highest setting, and coated. Then, the treated polymer was placed in a blade dryer and left for 10 minutes at a temperature of 110° C.

The product passed the 3 h anti-caking test. Its retention and AUL are shown in Table 2.

Example 21

0.5 g of ethylene carbonate, 0.5 g of acetone, 2 g of water, 0.075 g of $ZnCl_2$ and 0.05 g of Imbentin CMEA/045 (Kolb AG) were mixed and added to 50 g of powder 3 using a syringe, stirring with a mixer (Krups Dry Mix Type 7007) on its highest setting. Then, the polymer was poured into a photographic tank and dried for 50 minutes in a circulating air drying oven at 170° C.

The treated polymer passed the 3 h anti-caking test. Its retention, AUL and surface tension are shown in Table 2.

Example 22

Powder 3 was coated by adding a mixture of 2% by weight of water and 1% by weight of $H_2SO_4$ (98%) with a syringe, stirring using a mixer. 0.5 g of ethylene carbonate, 0.5 g of acetone, 0.05 g of Imbentin CMEA/045 and 1 g of water were mixed together and added using a syringe to 50 g of powder 3 stirring with the mixer (Krups Dry Mix Type 7007) on its highest setting. Then, the polymer was poured into a photographic tank and dried for 50 minutes in a circulating air drying oven at 170° C.

The treated polymer passed the 3 h anti-caking test. Its retention, AUL and surface tension are shown in Table 2.

Example 23

0.5 g of ethylene carbonate, 0.5 g of acetone, 1 g of water, 1 g of $H_3PO_4$ (85%) and 0.1 g of Imbentin CMEA/045 (Kolb AG) were mixed together and added using a syringe to 50 g of powder 3 stirring with the mixer (Krups Dry Mix Type 7007) on its highest setting. Then, the polymer was poured into a photographic tank and dried for 50 minutes in a circulating air drying oven at 170° C.

The treated polymer passed the 3 h anti-caking test. Its retention, AUL and surface tension are shown in Table 2.

Examples 24-27

Examples 24-29 were carried out as described for Example 21, with the amounts of Lewis acids and Imbentin CMEA/045 employed shown in Table 2. The results of the 3 h anti-caking tests, retention, AUL and surface tension for the respective polymers are shown in Table 2.

TABLE 2

| Example | Lewis acid | Imbentin*/ Lewis acid** (Gew. %) | Temp./ time (° C./min) | Retention (g/g) | $AUL_{0.9\,psi}$ (g/g) | 3 h Anti-caking |
|---|---|---|---|---|---|---|
| Comp. Ex. 4 | $Al_2(SO_4)_3 \times 18H_2O$ | 0.0/0.50 | 170/50 | 31.5 | 22.6 | − |
| 20 | $Al_2(SO_4)_3 \times 14H_2O$ | 0.2/0.20 | 110/10 | 35.7 | 7.2 | + |
| 21 | $ZnCl_2$ | 0.1/0.15 | 170/50 | 32.8 | 21.8 | + |
| 22 | $H_2SO_4$ | 0.1/1.00 | 170/50 | 31.9 | 19.0 | + |
| 23 | $H_3PO_4$ | 0.2/2.00 | 170/50 | 30.0 | 17.1 | + |

TABLE 2-continued

| Example | Lewis acid | Imbentin*/ Lewis acid** (Gew. %) | Temp./ time (° C./min) | Retention (g/g) | $AUL_{0.9\,psi}$ (g/g) | 3 h Anti-caking |
|---|---|---|---|---|---|---|
| 24 | $FeCl_3 \times 6H_2O$ | 0.1/0.05 | 170/50 | 32.3 | 21.4 | + |
| 25 | $MgSO_4 \times 7H_2O$ | 0.3/0.10 | 170/50 | 31.5 | 23.6 | + |
| 26 | $AlCl_3 \times 6H_2O$ | 0.1/0.05 | 160/50 | 35.9 | 14.0 | + |
| 27 | $FeCl_3 \times 6H_2O$ | 0.2/0.10 | 170/50 | 32.1 | 19.2 | + |

*Imbentin CMEA/045
**with respect to component I
+: anti-caking test passed
−: anti-caking test failed

Examples 28-29

0.5 g of ethylene carbonate, 2 g of water, aluminium sulphate and Imbentin CMEA/045 (Kolb AG) were mixed together and added using a syringe to 50 g of powder 3 stirring with the mixer (Krups Dry Mix Type 7007) on its highest setting. Then, the polymer was poured into a photographic tank and dried for 50 minutes in a circulating air drying oven at 170° C. The reaction conditions and product properties are shown in Table 3.

Examples 30-33

Two polyacrylic acids were produced with a degree of neutralisation of 65% or 70% and a retention of 34% or 32 g/g in 0.9% aqueous NaCl solution as described for the production of powder 1.50 g of this powder (particle size in the range 150 to 850 μm) was mixed with a mixture consisting of 0.5 g of ethylene carbonate, 2 g of water, aluminium sulphate× $14H_2O$ and Imbentin CMEA/045 using a mixer (Krups Dry Mix Type 7007) on its highest setting. The powder was then dried in a circulating air drying oven in a photographic tank. The reaction conditions and properties of the products are shown in Table 3.

surface coating component I with a coating agent selected from the group consisting of nitrogen-containing, non-ionic surfactants as component II and optionally a Lewis acid as component III; wherein said surfactant has the general formula I:

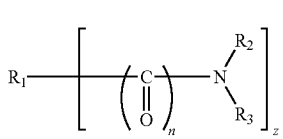

in which
$R_1$ is an aliphatic $C_1$ to $C_{30}$ hydrocarbon z-substituted aliphatic residue,
$R_2$ is selected from a hydrogen, an $C_2$ to $C_{24}$ aliphatic hydrocarbon residue, and
a hydroxyalkylene residue
$R_3$, which may be identical or different, has the same meaning as $R_2$, provided that with amide compounds, at least one of residues $R_2$ or $R_3$ represents a hydroxyalkylene residue or an alkoxylated hydroxyalkylene residue

TABLE 3

| Ex. | Start product DN | Retention g/g | Imbentin[1] | $Al_2(SO_4)_3 \times 14H_2O$[1] | Temp. ° C. | Time min | Anti-caking test[2] | Retention | AUL 0.9 psi g/g |
|---|---|---|---|---|---|---|---|---|---|
| 28 | 70 | 39 | 0.1 | 0.1 | 170 | 60 | 6 | 31.7 | 22.0 |
| 29 | 70 | 39 | 0.1 | 0.2 | 170 | 60 | 6 | 31.6 | 21.5 |
| 30 | 65 | 34 | 0.25 | 0.45 | 170 | 60 | 24 | 30 | 20.5 |
| 31 | 65 | 34 | 0.25 | 0.50 | 170 | 60 | 24 | 30 | 21 |
| 32 | 70 | 32 | 0.30 | 0.50 | 180 | 30 | 24 | 28 | 19.5 |
| 33 | 70 | 32 | 0.25 | 0.60 | 180 | 30 | 24 | 30 | 20 |

[1]Wt % with respect to powder
[2]Anti-caking test passed after 6 or 24 hours

What is claimed is:

1. A process for the production of superabsorbent polymer powder with a reduced caking tendency in a moist environment and/or at high temperatures, comprising the steps of:
providing a component I which is a water- or aqueous fluid-absorbing, dried, surface-cross-linked polymer powder based on polymerized monomers containing at least partially neutralized acid groups wherein the polymerized monomers is formed into a gel which was dried for about 90 minutes at about 150° C. and the dried polymer was ground and screened to a polymer powder and coating the polymer powder with a surface cross-linking agent to form the water- or aqueous fluid-absorbing, dried, polymer powder coated with a surface cross-linking agent of component I; and or a corresponding esterified or alkoxylated or esterified and alkoxylated hydroxyalkylene residue with the definition given for $R_2$ above;
n is 1; and z is a whole number from 1 to 4
heat treating the surface coated component I at a temperature of from 100° C. to 250° C. to cause component I to react with the surface cross-linking agent, the coating agent component II and optionally component III;
wherein the superabsorbent polymer powder passes the Anti-caking test as set forth herein.

2. The process according to claim 1, further comprising the step of mixing an aqueous solution of the coating agent(s) with component I.

3. The process according to claim 1, further comprising the step of treating the polymer before, during, or after its surface cross-linking with an aqueous solution of component II and optional component III, with the addition of heat.

4. The process according to claim 1, further comprising the step of simultaneously transforming the aqueous solution of component II and optional component III and surface cross-linking the polymer.

5. The process according to claim 1 wherein said nitrogen-containing, non-ionic surfactant is selected from stearylamine, ethoxylated with 10 ethylene oxide (EO) units, coconut acid diethanolamide, lauric acid diethanolamide, coconut acid monoethanolamide, laurylamine, ethoxylated with 10 EO units, oleylamine ethoxylated with 20 EO units, oleic acid monoethanolamide ethoxylated with 3 EO units, oleic acid monoethanolamide, ethoxylated with 6 EO units, Oleic acid monoethanolamide ethoxylated with 14 EO units, or coconut acid monoethanolamide ethoxylated with 4.5 EO.

6. The process according to claim 1 wherein said component III is selected from aluminum sulfate, aluminum chloride, zinc acetate, zinc chloride, zinc sulfate, iron chloride, magnesium sulfate, magnesium chloride, sulphuric acid, sulphur-containing acids, selenic acid, nitric acid, phosphonic acid or phosphorus-containing acids acetic acid, oxalic acid, lactic acid, citric acid, tartaric acid or hydrated forms of aluminum sulfate, aluminum chloride, zinc acetate, zinc chloride, zinc sulfate, and iron chloride.

7. The process according to claim 6 wherein said aluminum sulfate is $Al_2(SO_4)_3 \times 14\text{-}18H_2O$, and aluminum chloride is $AlCl_3 \times 6H_2O$; zinc acetate is $Zn(CH_3COO)_2 \times 2H_2O$.

8. A superabsorbent polymer powder produced by the process defined in claim 1.

9. The superabsorbent polymer powder of claim 8 having a Retention of from 20 g/g to 36 g/g according to the Retention Test Method and a fluid uptake under load at 0.9 psi (AUL0.9 psi) of from 15 g/g to 40 g/g according to the Fluid Uptake under 0.9 psi load AUL Test Method.

10. A process for the production of superabsorbent polymer powder with a reduced caking tendency comprising the steps of:
   a) preparing a superabsorbent polymer gel including polymerizing polymerized monomers containing at least partially neutralized acid groups and at least one crosslinker;
   b) drying the superabsorbent polymer gel to form a dried superabsorbent polymer;
   c) grinding and screening the dried superabsorbent polymer to have a particle size in the range from 150 to 850 µm;
   d) treating the dried superabsorbent polymer of step c) with a surface cross-linking agent to form a water- or aqueous fluid-absorbing, dried, surface-cross-linked polymer powder, referred to as component I; and
   e) surface coating the water- or aqueous fluid-absorbing, dried, surface-cross-linked polymer powder of step d) with a coating agent selected from the group consisting of nitrogen-containing, non-ionic surfactant and optionally a Lewis acid; wherein said surfactant has the general formula I:

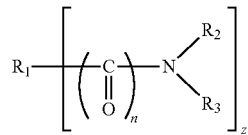

in which
   $R_1$ is an aliphatic $C_1$ to $C_{30}$ hydrocarbon z-substituted aliphatic residue,
   $R_2$ is selected from a hydrogen, an $C_2$ to $C_{24}$ aliphatic hydrocarbon residue, and
   a hydroxyalkylene residue
   $R_3$, which may be identical or different, has the same meaning as $R_2$, provided that with amide compounds, at least one of residues $R_2$ or $R_3$ represents a hydroxyalkylene residue or an alkoxylated hydroxyalkylene residue or a corresponding esterified or alkoxylated or esterified and alkoxylated hydroxyalkylene residue with the definition given for $R_2$ above;
   n is 1; and z is a whole number from 1 to 4; and
   f) heat treating the surface coated water- or aqueous fluid-absorbing, dried, surface-cross-linked polymer powder of step e) at a temperature of from 100° C. to 250° C. to cause surface coated water- or aqueous fluid-absorbing, dried, surface-cross-linked polymer powder to react with the surfactant and optionally, the Lewis acid to form the superabsorbent polymer powder;
   wherein the superabsorbent polymer powder passes the Anti-caking Test as set forth herein.

11. The process according to claim 10 wherein said surfactant is selected from stearylamine, ethoxylated with 10 ethylene oxide (EO) units, coconut acid diethanolamide, lauric acid diethanolamide, coconut acid monoethanolamide, laurylamine, ethoxylated with 10 EO units, oleylamine ethoxylated with 20 EO units, oleic acid monoethanolamide ethoxylated with 3 EO units, oleic acid monoethanolamide, ethoxylated with 6 EO units, Oleic acid monoethanolamide ethoxylated with 14 EO units, or coconut acid monoethanolamide ethoxylated with 4.5 EO.

12. The process according to claim 10 wherein said coating agent further includes a Lewis acid selected from is selected from aluminum sulfate, aluminum chloride, zinc acetate, zinc chloride, zinc sulfate, iron chloride, magnesium sulfate, magnesium chloride, sulphuric acid, sulphur-containing acids, selenic acid, nitric acid, phosphonic acid or phosphorus-containing acids acetic acid, oxalic acid, lactic acid, citric acid, tartaric acid or hydrated forms of aluminum sulfate, aluminum chloride, zinc acetate, zinc chloride, zinc sulfate, and iron chloride.

13. A superabsorbent polymer powder produced by the process defined in claim 10.

14. The superabsorbent polymer powder of claim 13 having a Retention of from 20 g/g to 36 g/g according to the Retention Test Method and a fluid uptake under load at 0.9 psi (AUL0.9 psi) of from 15 g/g to 40 g/g according to the Fluid Uptake under 0.9 psi load AUL Test Method.

* * * * *

UNITED STATES PATENT AND TRADEMARK OFFICE
CERTIFICATE OF CORRECTION

| | | |
|---|---|---|
| PATENT NO. | : 8,247,640 B2 | Page 1 of 1 |
| APPLICATION NO. | : 12/718617 | |
| DATED | : August 21, 2012 | |
| INVENTOR(S) | : Gerd Jonas, Richard Mertens and Markus Frank | |

It is certified that error appears in the above-identified patent and that said Letters Patent is hereby corrected as shown below:

Column 8,
Line 20, "component Ito react" should read -- component I to react --.

Line 25, "cause component to react" should read -- cause component I to react --.

Signed and Sealed this
Sixteenth Day of October, 2012

David J. Kappos
*Director of the United States Patent and Trademark Office*